USOO5648239A

United States Patent [19]

Hawkins et al.

[11] Patent Number: 5,648,239

[45] Date of Patent: Jul. 15, 1997

[54] HUMAN CAMP-DEPENDENT PROTEIN KINASE INHIBITOR HOMOLOG

[75] Inventors: Phillip R. Hawkins, Mountain View; Jennifer L. Hillman, San Jose; Janice Au-Young, Berkeley, all of Calif.

[73] Assignee: Incyte Pharmaceuticals, Inc., Palo Alto, Calif.

[21] Appl. No.: 667,679

[22] Filed: Jun. 21, 1996

[51] Int. Cl.$^6$ .................. C12N 15/00; C12N 15/85; C12N 15/63; C12N 15/11

[52] U.S. Cl. .............. 435/69.2; 435/419; 435/320.1; 435/348; 435/325; 435/358; 435/367; 435/369; 536/23.5

[58] Field of Search .................. 536/23.5; 435/320.1, 435/240.2, 252.3, 252.33, 69.2

[56] References Cited

PUBLICATIONS

Olsen SR, et al. "Isolation and characterization of cDNA clones for an inhibitor protein of cAMP-dependent protein kinases." JBC 266 (17): 11158–11162 1991.

Baude et al., Evidence for the Importance of Hydrophobic Residues in the Interactions between the cAMP-dependent Protein Kinase Catalytic Subunit and the Protein Kinase Inhibitors, *J. Biol. Chem.*, 1996, 269:18128–18133.

Drumm et al., Molecular Biology of Cystic Fibrosis, *Mol. Genet Med.*, 1993, 3:33–68.

Marchetto et al., Cloning and sequencing of the cDNA encoding the avian kidney cAMP–dependent protein kinase inhibitor protein, *Gene*, 1995, 158:303–304.

Wang et al., Specific Processing of Native and Phosphorylated τ Protein by Proteases, Biochem. Biophys. Res. Com., 219:591–597.

Wen et al., The Expression and Intracellular Distribution of the Heat–stable Protein Kinase Inhibitor Is Cell Cycle Regulated, *J. Biol. Chem.*, 1995 270(5):2041–2046.

*Primary Examiner*—George C. Elliott
*Assistant Examiner*—Amy J. Nelson
*Attorney, Agent, or Firm*—Lucy J. Billings; Incyte Pharmaceuticals, Inc.

[57] ABSTRACT

The present invention provides a polynucleotide (ipka) which identifies and encodes a novel human cAMP-dependent protein kinase A inhibitor homolog (IPKA). The invention provides for genetically engineered expression vectors and host cells comprising the nucleic acid sequence encoding IPKA.

5 Claims, 5 Drawing Sheets

```
                11          20          29          38          47          56
5' CGC TGC GGG TTG CGG GCT GCG GGC GCT AGG CTG CCC CGG GGA GGC GCT GCG GAC 65          74          83          92         101         110
   CGG CGG CCC AGG CAC GGA GAG GCG GCG AGA CCG CAG AAT TCC CGT ACT GAT TAG 119         128         137         146         155         164
   TCA ACA GTG GAA AAT CTG AAG AGA TGC AAG CAG GAA AAA GAA ATT AAA CCA GGC 173         182         191         200         209         218
   CTG AGG AGC GAT GCG ACA GGC ATG ATG GAG GTC GAG TCC TCC TAC TCG GAC TTC
                                    M   M   E   V   E   S   S   Y   S   D   F 227         236         245         254         263         272
   ATC TCC TGT GAC CGG ACA GGC CGT CGG AAT GCG GTC CCT GAC ATC CAG GGA GAC
    I   S   C   D   R   T   G   R   R   N   A   V   P   D   I   Q   G   D 281         290         299         308         317         326
   TCA GAG GCT GTG AGC GTG AGG AAG CTG GCT GGA GAC ATG GGC GAG CTG GCA CTC
    S   E   A   V   S   V   R   K   L   A   G   D   M   G   E   L   A   L 335         344         353         362         371         380
   GAG GGG GCA GAA GGA CAG GTG GAG GGA AGC GCC CCA GAC AAG GAA GCT GGC AAC
    E   G   A   E   G   Q   V   E   G   S   A   P   D   K   E   A   G   N 389         398         407         416         425         434
   CAG CCC CAG AGC AGC GAT GGG ACC ACC TCG TCT TGA ATC TGA CCT TGT CCA AGA
    Q   P   Q   S   S   D   G   T   T   S   S 443         452         461         470         479         488
   AGG CTG GAC GAG AGA CCT TCT GTC CCC TCC CAG AGG GGG AAC CCT GGC ACT GGC 497         506         515         524         533         542
   CCA GCA GCC TCT TCT CTG AGC TCC ATG TCC CAG ATA AAC CAG GCC AGA CTG AGA

AGG 3'
```

FIG. 1

The Electronic Northern for Clone: 932876
and Stringency = 50

| Library | Lib Description | Abun | Pct Abun |
|---------|-----------------|------|----------|
| HUVENOB01 | HUVEC endothelial cell line, control | 4 | 0.168 |
| PROSNOT07 | prostate, 69 M, match to PROSTUT05 | 2 | 0.070 |
| COLNNOT16 | colon, sigmoid, 62 M | 2 | 0.059 |
| CERVNOT01 | cervix, 35 F | 3 | 0.058 |
| LUNGAST01 | lung, asthma, 17 M | 3 | 0.045 |
| MUSCNOT02 | muscle, psoas, 12 M | 1 | 0.038 |
| HUVESTB01 | HUVEC endothelial cell line, shear stress | 1 | 0.036 |
| SCORNON02 | spinal cord, 71 M, NORM | 1 | 0.035 |
| LUNGNOT01 | lung, 72 M | 1 | 0.034 |
| COLNNOT05 | colon, 40 M, match to COLNCRTOI | 1 | 0.029 |
| PLACNOM02 | placenta, neonatal F, NORM, WM | 5 | 0.028 |
| BRAINOM03 | brain, 55 M, NORM, WM | 1 | 0.027 |
| COLNTUT02 | colon tumor, 75 M, match to COLNNOT01 | 1 | 0.022 |
| ADENINB01 | adenoid, inflamed, 3 yr old | 1 | 0.019 |
| LUNGTUT02 | lung tumor, metastasis, 79 M, match to LUNGNOT03 | 1 | 0.019 |
| SYNORAT04 | synovium, wrist, rheumatoid, 62 F | 1 | 0.017 |
| BRSTNOT02 | breast, 55 F, match to BRSTTUT01 | 1 | 0.016 |
| BRSTTUT03 | breast tumor, 58 F, match to BRSTNOT05 | 1 | 0.015 |
| MELANOM01 | melanocytes, M, NORM, WM | 1 | 0.013 |
| LIVSFEM02 | liver/spleen, fetal M, NORM, WM | 3 | 0.009 |

The Northern Link Info returned a total of 20 results.

FIG. 2

```
  1 M M E V E S S Y S D F I S C D R T G R R N A V P D I Q G D S   IPKA
  1 M T D V E S T Y A D F I A S G R T G R R N A L H D I L V S S   GI 632652
  1 M T D V E T T Y A D F I A S G R T G R R N A I H D I L V S S   GI 243494

31 E A V S V R K L A G D M G E L A L E G A E G Q V E G S A P D   IPKA
 31 P G G N S S E L A L K L S E L D I N K A E G D A Q R N P       GI 632652
 31 A S G N S N E L A L K L A G L D I N K T E G E E D A Q R S S   GI 243494

61 K E A G N O P Q S S D G T T S S                               IPKA
 61 S E Q T G E A Q G E A A K Q E S                               GI 632652
 61 T E Q S G E A Q G E A A K S E S                               GI 243494
```

FIG. 3

HUMAN CAMP-DEPENDENT PROTEIN KINASE INHIBITOR HOMOLOG

FIELD OF THE INVENTION

The present invention relates to nucleic acid and amino acid sequences of a novel human cAMP-dependent protein kinase inhibitor homolog and to the use of these sequences in the diagnosis, study, prevention and treatment of disease.

BACKGROUND OF THE INVENTION

The cAMP-dependent protein kinase (PKA), the prime target of the second messenger cAMP in mammalian cells, is activated by the binding of cAMP to the regulatory subunit (R), of the molecule and results in the release of the active catalytic kinase subunit (C). There are several isoforms of both subunits of PKA. All members of the PKA family share significant sequence homology and perform signal transduction via protein phosphorylation. Almost all cell types express one or more isoforms of PKA. The protein inhibitor of PKA (PKI) acts by binding with high affinity to the substrate binding site of the free active catalytic subunit (Walsh D. A. (1990) Peptides and Protein Phosphorylation, CRC, Boca Raton, Fla., pp. 43–84). In addition, PKI has been shown to export the C subunit from the nucleus (Fantozzi D. A. et al (1994) J Biol Chem 269: 2676–2686).

The endogenous inhibitor of cAMP-dependent protein kinase (PKA) is down-regulated in the kidneys from vitamin-D-replete chicks as compared to vitamin-D-deficient chicks. Screening of a vitamin-D-deficient chick kidney library resulted in the isolation of a 450-bp cDNA clone encoding the 76-amino acid protein kinase inhibitor (Marchetto G. S. and Henry H. L. (1995) Gene 158: 303–304). The deduced amino acid sequence of avian PKI shares 80% and 41% identity with the mammalian PKI alpha and PKI beta 1 isoforms, respectively.

Both avian PKI and human PKI alpha share conserved N-terminal sequences, including the pseudo-substrate site (18GRRNA22), which are required for potent inhibition of the catalytic subunit of PKA (Marchetto and Henry, supra). The amino acid phenylalanine at position 11 plays a critical role in PKI-C subunit binding (Baude et al (1994) J Biol Chem 269: 18128–18133).

Cell cycle synchrony studies suggests that PKI has an important role in the inhibition of nuclear C subunit activity that is required for cell cycle progression (Wen W. et al (1995) J Biol Chem 270: 2041–2046). Microinjection of PKI alpha antibody prevented the cell cycle progression of serum-starved cells.

Disease and PKA

Human airway smooth muscle (ASM) contains beta 2-adrenergic receptors which, when stimulated, cause a rise in intracellular cAMP and activation of PKA, which in turn phosphorylates several cellular proteins, resulting in relaxation (Barnes P. J. (1993) Life Sci 52: 2101–2109). Activated PKA also acts in ASM cell proliferation, which contributes to increased airway resistance in bronchial asthma. Vasoactive intestinal peptide (VIP) selectively and potently inhibits human airway smooth muscle cell growth and multiplication, and nullifies the mitogenic effect of histamine, by a PKA-mediated mechanism. A deficiency of VIP may lead to ASM hyperplasia due to unopposed stimulation by endogenous mitogens. A selective inhibitor of PKA abolished the inhibitory effect of VIP (Maruno K. et al (1995) Am J Physiol 268: 1047–1051 ).

Cystic fibrosis is caused by a mutation in the CFTR gene. CFTR, a chloride conducting membrane protein, is a substrate for PKA phosphorylation. This phosphorylation has been determined to be a step in the activation pathway (Drumm M. L. and Collins F. S. (1993) Mol Genet Med 3: 33–68).

Systemic lupus erythematosus (SLE) is an autoimmune disorder of indeterminate etiology characterized by a dysfunctional cellular immune response. T lymphocytes from subjects with active systemic lupus erythematosus exhibit reduced cAMP-inducible, PKA-dependent protein phosphorylation of several intracellular substrates compared with healthy and disease controls. Intact T cells from patients with severe SLE disease activity are impaired in PKA-catalyzed protein phosphorylation (Kammer G. M. et al (1994) J Clin Invest 94: 422–430). Variation in the concentration of PKA activity is an important element in modulating T cell proliferative responses. Induction of PKA activity in T cells inhibits anti-CD3 monoclonal antibody-induced T cell proliferation (Bauman G. P. et al (1994) Cell Immunol 158: 182–194).

The development of cross-resistance to many chemotherapeutic drugs, termed multidrug resistance (MDR), is one of the major reasons why cancer chemotherapy ultimately fails. MDR is often associated with over-expression of the MDR1 gene product, P-glycoprotein, a multifunctional drug transporter. MDR1 expression can be modulated by PKA, opening up the possibility of modulating MDR by selectively down-regulating the activity of PKA-dependent transcription factors which upregulate MDR1 expression. High levels of type I PKA occur in primary breast carcinomas and patients exhibiting this phenotype show decreased survival (Glazer R. I. and Rohlff C. Breast Cancer Res Treat (1994) 31: 263–271). The selective PKA inhibitors, 8-Cl-cAMP and Rp8-Cl-cAMP[S] may be particularly useful for downregulating PKA-dependent MDR-associated transcription factors. These compounds downregulate transient expression of a reporter gene under the control of several MDR1 promoter elements (Glazer and Rohlff, supra). 8-Cl-cAMP has recently been shown to decrease MDR1 expression in multidrug-resistant human breast cancer cells (Scala S. et al (1995) J Clin Invest 96:1026–1034).

PKA participates in the sequence of molecular events that underlie learning and memory. A peptide inhibitor of PKA disrupts associative learning when expressed in transgenic fruit flies (Drain P. et al (1991) Neuron 6: 71–82). In mammalian systems, inhibitors of PKA were found to block hippocampal long-term potentiation, which is thought to be a mechanism for the establishment of explicit memory (Frey U. et al (1993) Science 260: 1661–1664). In Alzheimer's disease, where memory loss is one of the earliest and most debilitating characteristics, tau proteins are phosphorylated by PKA. Tau degradation has been implicated in the pathogenesis of Alzheimer's disease and PKA phosphorylation of tau affects the rate of proteolytic degradation (Wang X. et al (1996) Biochem Bioph Res Commun 219: 591–597).

PKA activity plays a role in many important biological systems. The selective inhibition of PKA may allow successful management of the diseases associated with PKA induced effects, such as cancer, memory disorders, and auto-immune diseases.

SUMMARY

The present invention relates to a novel human cAMP-dependent protein kinase A inhibitor homolog, IPKA, initially identified among the partial cDNAs from a cervix tissue library (CERVNOT01) and to the use of the nucleic acid and amino acid sequences disclosed herein in the study, diagnosis, prevention and treatment of disease. Nucleic acid encoding a portion of IPKA was also found in cDNA libraries in tissues from tumors, lung of an asthma patient, placenta, umbilical cord endothelium, colon, and cervix.

Nucleic acid encoding a portion of IPKA was first identified in the cDNA, Incyte Clone 932876 (SEQ ID NO: 1), through a computer-generated search for amino acid sequence alignments. The nucleic acid sequence, SEQ ID NO: 1; disclosed herein and designated in lower case, ipka; encodes the amino acid sequence, SEQ ID NO: 2, designated in upper case, IPKA. The present invention is based, in part, on the chemical and structural homology between IPKA and avian PKI (GI 632652; Marchetto and Henry, supra). IPKA has 37% identity to avian PKI. As illustrated by FIGS. 4 and 5, IPKA and GI 632652 have similar hydrophobicity plots suggesting shared configuration and activity. In addition, IPKA has 33% identity to human PKI alpha (GI 243494; Olsen S. R. and Uhler M. D. (1991) Mol Endocrinol 5: 126–1256). IPKA shares with both avian PKI and human PKI alpha conserved N-terminal sequences, including the pseudo-substrate site (amino acids: 18GRRNA22) and phenylalanine at position 11. These sequences are critical for binding and inhibition of PKA subunit C. The novel IPKA is 76 amino acids long and lacks obvious glycosylation sites.

The nucleic acid sequence, oligonucleotides, peptide nucleic acids (PNA), fragments, portions or antisense molecules thereof, may be used in diagnostic assays of body fluids or biopsied tissues to detect the expression level of ipka. For example, ipka sequences designed from SEQ ID NO:1 can be used to detect the presence of the mRNA transcripts in a patient or to monitor modulation of the transcripts during treatment.

The present invention relates, in part, to the inclusion of the polynucleotide encoding IPKA in an expression vector which can be used to transform host cells or organisms. Such transgenic hosts are useful for the production of IPKA. Purified IPKA or fragments of IPKA may be useful as a pharmaceutical composition. For example, they may be used to inhibit or reverse the development of tumors.

The ipka nucleic acid sequence also provides for the design of antisense molecules useful in diminishing or eliminating expression of the genomic nucleotide sequence in breast or other cancers where IPKA activity may hinder a desired activity of PKA.

The invention further provides diagnostic assays and kits for the detection of naturally occurring IPKA. It provides for the use of purified IPKA as a positive control and to produce anti-IPKA antibodies which can be used to quantitate the amount of IPKA in human body fluids or biopsied tissues. IPKA can also be used to identify agonists which induce the production of or prolong the lifespan of the IPKA molecule in vivo or in vitro.

The invention comprises pharmaceutical compositions comprising IPKA, ipka antisense molecules capable of disrupting expression of the genomic sequence, and agonists, antibodies, antagonists or inhibitors of the IPKA. These compositions are useful for the prevention or treatment of conditions associated with expression of IPKA or of PKA.

DESCRIPTION OF THE FIGURES

FIG. 1 displays the nucleic acid sequence (SEQ ID NO:1) and deduced amino acid sequence (SEQ ID NO:2) of the human PKI homolog, IPKA. The alignment of the sequences was produced using MacDNAsis software (Hitachi Software Engineering Co Ltd).

FIG. 2 shows the northern analysis for Incyte Clone 932876 (SEQ ID NO:1). The northern analysis was produced electronically using LIFESEQ™ database (Incyte Pharmaceuticals, Palo Alto, Calif.) and shows cDNA libraries in which ipka was expressed and the percentage abundance at which ipka is expressed. The percentage abundance is defined as 100 times the number of ipka transcripts found in the library divided by the total number of transcripts in the library.

FIG. 3 shows the amino acid sequence alignments among IPKA (SEQ ID NO:2), avian PKI (GI 293273; SEQ ID NO:3), and human PKI alpha (GI 862933; SEQ ID NO:4). Sequences were aligned using the multisequence alignment program of DNAStar software (DNAStar Inc, Madison, Wis.).

In FIGS. 4 and 5, the X axis reflects amino acid position, and the negative Y axis, hydrophobicity. The hydrophobicity plots were generated using MacDNAsis software.

FIG. 5 shows the hydrophobicity plot for avian PKI, SEQ ID NO:3.

DETAILED DESCRIPTION OF THE INVENTION

Figure 4:
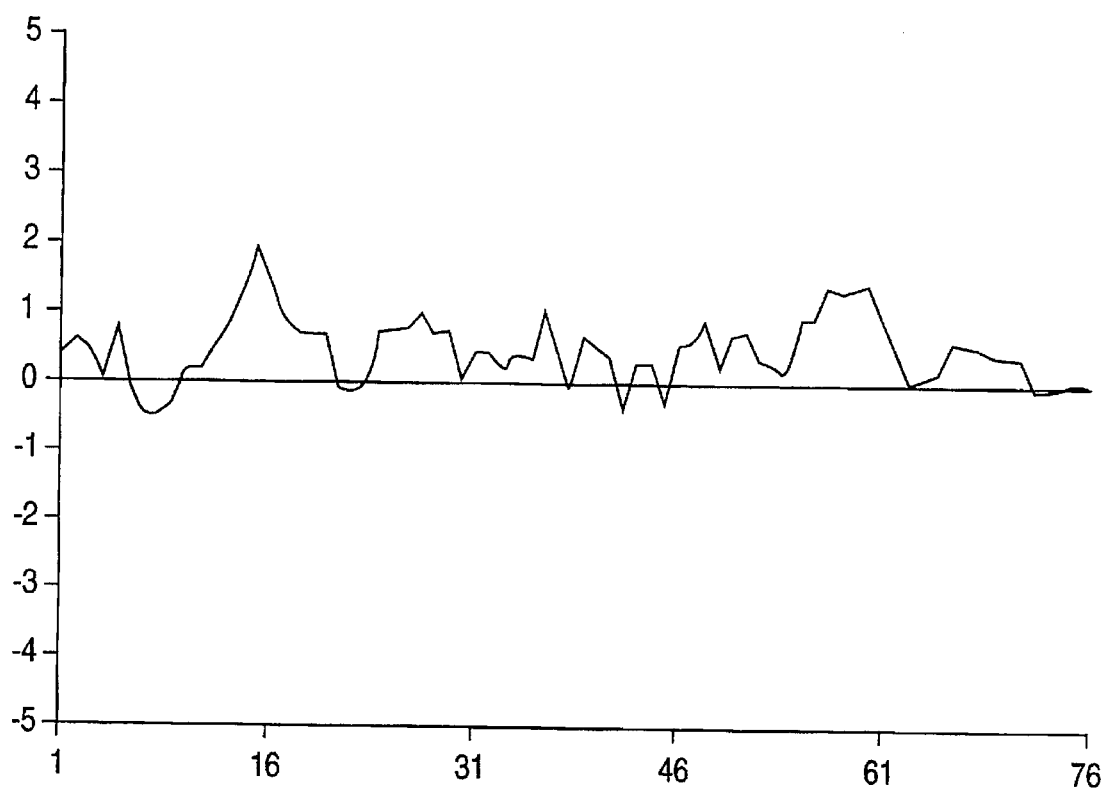
FIG. 4 shows the hydrophobicity plot for IPKA, SEQ ID NO:2.

The present invention relates to a novel human protein kinase A inhibitor initially identified among the cDNAs from a cervix tissue library (CERVNOT01) and to the use of the nucleic acid and amino acid sequences in the study, diagnosis, prevention and treatment of disease.

Nucleic acid encoding IPKA was first identified in cDNA, Incyte Clone 932876 (SEQ ID NO: 1), through a computer-generated search for amino acid sequence alignments. The ipka nucleic acid sequence, SEQ ID NO: 1, encodes the IPKA amino acid sequence, SEQ ID NO: 2. The present invention is based, in part, on the chemical and structural homology between IPKA and the protein kinase A inhibitor homolog (GI 632652; Marchetto and Henry, supra) and identity between IPKA and human PKI alpha (GI 243494; Olsen S. R. and Uhler M. D., supra). IPKA has 37% identity to arian PKI and 33% identity to human PKI alpha. IPKA and avian PKI have similar hydrophobicity suggesting shared configuration and activity. The novel IPKA is 76 amino acids long and lacks obvious glycosylation sites. Through northern analysis using the LIFESEQ™ database of human gene sequence and expression information (Incyte Pharmaceuticals, Palo Alto, Calif.) ipka sequences were found to be most abundant in tissues flora tumors, lung of an asthma patient, placenta, umbilical cord endothelium, colon, and cervix.

As used herein, IPKA refers to the amino acid sequence of IPKA from any species, particularly mammalian, including bovine, ovine, porcine, murine, equine, and preferably human, in a naturally occurring form or from any source whether natural, synthetic, semi-synthetic or recombinant. As used herein, "naturally occurring" refers to an amino acid sequence which is found in nature.

The present invention also encompasses IPKA variants. A preferred IPKA variant is one having at least 80% amino acid sequence similarity, a more preferred IPKA variant is one having at least 90% amino acid sequence similarity and a most preferred IPKA variant is one having at least 95% amino acid sequence similarity to the IPKA amino acid sequence (SEQ ID NO:2).

The nucleic acid sequence, oligonucleotides, fragments, portions or antisense molecules thereof, may be used in diagnostic assays of body fluids or biopsied tissues to detect the expression level of ipka. For example, ipka sequences designed from the sequence (SEQ ID NO:1) can be used to detect the presence of the mRNA transcripts in a patient or to monitor the modulation of transcripts during treatment.

The present invention relates, in part, to the inclusion of the polynucleotide encoding IPKA in an expression vector which can be used to transform host cells or organisms. Such transgenic hosts are useful for the production of IPKA.

The nucleic acid sequence also provides for the design of antisense molecules useful in diminishing or eliminating expression of the genomic nucleotide sequence in tumor or cancer cells.

IPKA can also be used in screening assays to identify agonists which induce the production of or prolong the lifespan of the IPKA molecule in vivo or in vitro. IPKA can be similarly used to screen for antagonists or inhibitors which bind IPKA. Such antagonists or inhibitors can be delivered into the vascular system or appropriate cell compartments to inhibit the activity of IPKA.

The invention also relates to pharmaceutical compositions comprising IPKA, or fragments thereof, ipka antisense molecules capable of disrupting expression of the naturally occurring gene, and agonists, antibodies, antagonists or inhibitors of IPKA. These compositions are useful for the prevention or treatment of conditions associated with abnormal expression of PKA.

"Nucleic acid sequence" as used herein refers to an oligonucleotide, nucleotide or polynucleotide, and fragments or portions thereof, and to DNA or RNA of genomic or synthetic origin which may be single- or double-stranded, and represent the sense or antisense strand. Similarly, amino acid sequence as used herein refers to an oligopeptide, peptide, polypeptide or protein sequence.

"Peptide nucleic acid" as used herein refers to a molecule which comprises an oligomer to which an amino acid residue, such as lysine, and an amino group have been added. These small molecules, also designated anti-gene agents, stop transcript elongation by binding to their complementary (template) strand of nucleic acid (Nielsen P. E. et al (1993) Anticancer Drug Des 8:53–63).

A "variant" of IPKA may have an amino acid sequence that is different by one or more amino acid "substitutions". The variant may have "conservative" changes, wherein a substituted amino acid has similar structural or chemical properties, eg, replacement of leucine with isoleucine. More rarely, a variant may have "nonconservative" changes, eg, replacement of a glycine with a tryptophan. Similar minor variations may also include amino acid deletions or insertions, or both. Guidance in determining which and how many amino acid residues may be substituted, inserted or deleted without abolishing biological or immunological activity may be found using computer programs well known in the art, for example, DNAStar software.

The term "biologically active" refers to a IPKA having structural, regulatory or biochemical functions of the naturally occurring IPKA. Likewise, "immunologically active" defines the capability of the natural, recombinant or synthetic IPKA, or any oligopeptide thereof, to induce a specific immune response in appropriate animals or cells and to bind with specific antibodies.

The term "derivative" as used herein refers to the chemical modification of a ipka or the encoded IPKA. Illustrative of such modifications would be replacement of hydrogen by an alkyl, acyl, or amino group. A IPKA derivative would encode a polypeptide which retains essential biological characteristics of natural IPKA.

As used herein, the term "purified" refers to molecules, either nucleic or amino acid sequences, that are removed from their natural environment and isolated or separated from at least one other component with which they are naturally associated.

The IPKA Coding Sequences

The nucleic acid and deduced amino acid sequences of IPKA are shown in FIG. 1. In accordance with the invention, any nucleic acid sequence which encodes the amino acid sequence of IPKA can be used to generate recombinant molecules which express IPKA. In a specific embodiment described herein, the sequence for ipka was first isolated as Incyte Clone 932876 from a cervix tissue cDNA library (CERVNOT01), disclosed in U.S. patent application Ser. No. 60/015,513 entitled "Polynucleotides and Polypeptides Derived from Human Cervix" by Gooding et al and filed Mar. 22, 1996, the disclosure of which is incorporated herein by reference.

It will be appreciated by those skilled in the art that as a result of the degeneracy of the genetic code, a multitude of IPKA-encoding nucleotide sequences, some bearing minimal homology to the nucleotide sequences of any known and naturally occurring gene may be produced. The invention has specifically contemplated each and every possible variation of nucleotide sequence that could be made by selecting combinations based on possible codon choices. These combinations are made in accordance with the standard triplet genetic code as applied to the nucleotide sequence of naturally occurring IPKA, and all such variations are to be considered as being specifically disclosed.

Although nucleotide sequences which encode IPKA and its variants are preferably capable of hybridizing to the nucleotide sequence of the naturally occurring ipka under appropriately selected conditions of stringency, it may be advantageous to produce nucleotide sequences encoding IPKA or its derivatives possessing a substantially different codon usage. Codons may be selected to increase the rate at which expression of the peptide occurs in a particular prokaryotic or eukaryotic expression host in accordance with the frequency with which particular codons are utilized by the host. Other reasons for substantially altering the nucleotide sequence encoding IPKA and its derivatives without altering the encoded amino acid sequences include the production of RNA transcripts having more desirable properties, such as a greater half-life, than transcripts produced from the naturally occurring sequence.

It is now possible to produce a DNA sequence, or portions thereof, encoding a IPKA and its derivatives entirely by synthetic chemistry, after which the synthetic gene may be inserted into any of the many available DNA vectors and cell systems using reagents that are well known in the art at the time of the filing of this application. Moreover, synthetic chemistry may be used to introduce mutations into a ipka sequence or any portion thereof.

Also included within the scope of the present invention are polynucleotide sequences that are capable of hybridizing to the nucleotide sequence of FIG. 1 under various conditions of stringency. Hybridization conditions are based on the melting temperature (Tm) of the nucleic acid binding complex or probe, as taught in Berger and Kimmel (1987, *Guide to Molecular Cloning Techniques, Methods in Enzymology*, Vol 152, Academic Press, San Diego, Calif.)

incorporated herein by reference, and confer may be used at a defined "stringency" as explained below.

"Maximum stringency" typically occurs at about Tm-5° C. (5° C. below the Tm of the probe); "high stringency" at about 5° C. to 10° C. below Tm; "intermediate stringency" at about 10° C. to 20° C. below Tm; and "low stringency" at about 20° C. to 25° C. below Tm. As will be understood by those of skill in the art, a maximum stringency hybridization can be used to identify or detect identical polynucleotide sequences while an intermediate (or low) stringency hybridization can be used to identify or detect similar or related polynucleotide sequences.

The term "hybridization" as used herein shall include "any process by which a strand of nucleic acid joins with a complementary strand through base pairing" (Coombs J. (1994) Dictionary of Biotechnology, Stockton Press, New York, N.Y.). Amplification as carried out in the polymerase chain reaction technologies described in Dieffenbach C. W. and G. S. Dveksler (1995, PCR Primer, a Laboratory Manual, Cold Spring Harbor Press, Plainview, N.Y.) and incorporated herein by reference may follow the process of hybridization.

A "deletion" is defined as a change in either nucleotide or amino acid sequence in which one or more nucleotides or amino acid residues, respectively, are absent.

An "insertion" or "addition" is that change in a nucleotide or amino acid sequence which has resulted in the addition of one or more nucleotides or amino acid residues, respectively, as compared to the naturally occurring ipka.

A "substitution" results from the replacement of one or more nucleotides or amino acids by different nucleotides or amino acids, respectively.

Altered ipka nucleic acid sequences which may be used in accordance with the invention include deletions, insertions or substitutions of different nucleotides resulting in a polynucleotide that encodes the same or a functionally equivalent IPKA. The protein may also show deletions, insertions or substitutions of amino acid residues which produce a silent change and result in a functionally equivalent IPKA. Deliberate amino acid substitutions may be made on the basis of similarity in polarity, charge, solubility, hydrophobicity, hydrophilicity, and/or the amphipathic nature of the residues as long as the biological activity of IPKA is retained. For example, negatively charged amino acids include aspartic acid and glutamic acid; positively charged amino acids include lysine and arginine; and amino acids with uncharged polar head groups having similar hydrophilicity values include leucine, isoleucine, valine; glycine, alanine; asparagine, glutamine; serine, threonine phenylalanine, and tyrosine.

Included within the scope of the present invention are alleles of ipka. As used herein, an "allele" or "allelic sequence" is an alternative form of ipka. Alleles result from a mutation, ie, a change in the nucleic acid sequence, and generally produce altered mRNAs or polypeptides whose structure or function may or may not be altered. Any given gene may have none, one or many allelic forms. Common mutational changes which give rise to alleles are generally ascribed to natural deletions, additions or substitutions of amino acids. Each of these types of changes may occur alone, or in combination with the others, one or more times in a given sequence.

Methods for DNA sequencing are well known in the art and employ such enzymes as the Klenow fragment of DNA polymerase I, Sequenase® (US Biochemical Corp, Cleveland, Ohio)), Taq polymerase (Perkin Elmer, Norwalk, Conn.), thermostable T7 polymerase (Amersham, Chicago, Ill.), or combinations of recombinant polymerases and proofreading exonucleases such as the ELONGASE Amplification System marketed by Gibco BRL (Gaithersburg, Md.). Preferably, the process is automated with machines such as the Hamilton Micro Lab 2200 (Hamilton, Reno, Nev.), Peltier Thermal Cycler (PTC200; MJ Research, Watertown, Mass.) and the ABI 377 DNA sequencers (Perkin Elmer).

Extending the Polynucleotide Sequence

The polynucleotide sequence of ipka may be extended utilizing partial nucleotide sequence and various methods known in the art to detect upstream sequences such as promoters and regulatory elements. Gobinda et al (1993; PCR Methods Applic 2:318–22) disclose "restriction-site" polymerase chain reaction (PCR) as a direct method which uses universal primers to retrieve unknown sequence adjacent to a known locus. First, genomic DNA is amplified in the presence of primer to a linker sequence and a primer specific to the known region. The amplified sequences are subjected to a second round of PCR with the same linker primer and another specific primer internal to the first one. Products of each round of PCR are transcribed with an appropriate RNA polymerase and sequenced using reverse transcriptase.

Inverse PCR can be used to amplify or extend sequences using divergent primers based on a known region (Triglia T. et al (1988) Nucleic Acids Res 16:8186). The primers may be designed using OLIGO® 4.06 Primer Analysis Software (1992; National Biosciences Inc, Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Capture PCR (Lagerstrom M. et al (1991) PCR Methods Applic 1:111–19) is a method for PCR amplification of DNA fragments adjacent to a known sequence in human and yeast artificial chromosome DNA. Capture PCR also requires multiple restriction enzyme digestions and ligations to place an engineered double-stranded sequence into an unknown portion of the DNA molecule before PCR.

Parker J. D. et al (1991; Nucleic Acids Res 19:3055–60), teach walking PCR, a method for targeted gene walking which permits retrieval of unknown sequence. PromoterFinder™ a new kit available from Clontech (Palo Alto, Calif.) uses PCR, nested primers and PromoterFinder libraries to walk in genomic DNA. This process avoids the need to screen libraries and is useful in finding intron/exon junctions.

Preferred libraries for screening for full length cDNAs are ones that have been size-selected to include larger cDNAs. Also, random primed libraries are preferred in that they will contain more sequences which contain the 5' and upstream regions of genes. A randomly primed library may be particularly useful if an oligo d(T) library does not yield a full-length cDNA. Genomic libraries are useful for extension into the 5' nontranslated regulatory region.

A new method for analyzing either the size or confirming the nucleotide sequence of sequencing or PCR products is capillary electrophoresis. Systems for rapid sequencing are available from Perkin Elmer, Beckman Instruments (Fullerton, Calif.), and other companies. Capillary sequencing employs flowable polymers for electrophoretic separation, four different fluorescent dyes (one for each nucleotide) which are laser activated, and detection of the emitted wavelengths by a charge coupled devise camera. Output/light intensity is converted to electrical signal using appropriate software (eg. Genotyper™ and Sequence Navigator™ from Perkin Elmer) and the entire process from loading of samples to computer analysis and electronic data display is computer controlled. Capillary electrophoresis is particularly suited to the sequencing of small pieces of DNA which might be present in limited amounts in a particular sample. The reproducible sequencing of up to 350 bp of M13 phage DNA in 30 min has been reported (Ruiz-Martinez M. C. et at (1993) Anal Chem 65:2851–8).

Expression of the Nucleotide Sequence

In accordance with the present invention, polynucleotide sequences which encode IPKA, fragments of the polypeptide, fusion proteins or functional equivalents thereof may be used in recombinant DNA molecules that direct the expression of IPKA in appropriate host cells. Due to the inherent degeneracy of the genetic code, other DNA sequences which encode substantially the same or a functionally equivalent amino acid sequence, may be used to clone and express IPKA. As will be understood by those of skill in the art, it may be advantageous to produce IPKA-encoding nucleotide sequences possessing non-naturally occurring codons. Codons preferred by a particular prokaryotic or eukaryotic host (Murray E. et al (1989) Nuc Acids Res 17:477–508) can be selected, for example, to increase the rate of IPKA expression or to produce recombinant RNA transcripts having desirable properties, such as a longer half-life, than transcripts produced from naturally occurring sequence.

The nucleotide sequences of the present invention can be engineered in order to alter a ipka coding sequence for a variety of reasons, including but not limited to, alterations which modify the cloning, processing and/or expression of the gene product. For example, mutations may be introduced using techniques which are well known in the art, eg, site-directed mutagenesis to insert new restriction sites, to alter glycosylation patterns, to change codon preference, to produce splice variants, etc.

In another embodiment of the invention, a natural, modified or recombinant ipka sequence may be ligated to a heterologous sequence to encode a fusion protein. For example, for screening of peptide libraries for inhibitors of IPKA activity, it may be useful to encode a chimeric IPKA protein that is recognized by a commercially available antibody. A fusion protein may also be engineered to contain a cleavage site located between a IPKA sequence and the heterologous protein sequence, so that the IPKA may be cleaved and purified away from the heterologous moiety.

In an alternate embodiment of the invention, the coding sequence of ipka could be synthesized, whole or in part, using chemical methods well known in the art (see Caruthers M. H. et al (1980) Nuc Acids Res Syrup Ser 215–23, Horn T. et al (1980) Nuc Acids Res Syrup Ser 225–32, etc). Alternatively, the protein itself could be produced using chemical methods to synthesize a IPKA amino acid sequence, whole or in part. For example, peptide synthesis can be performed using various solid-phase techniques (Roberge J. Y. et al (1995) Science 269:202–204) and automated synthesis may be achieved, for example, using the ABI 431A Peptide Synthesizer (Perkin Elmer) in accordance with the instructions provided by the manufacturer.

The newly synthesized peptide can be purified by preparative high performance liquid chromatography (eg, Creighton (1983) Proteins, Structures and Molecular Principles, W. H. Freeman and Co, New York, N.Y.). The composition of the synthetic peptides may be confirmed by amino acid analysis or sequencing (eg, the Edman degradation procedure; Creighton, supra). Additionally the amino acid sequence of IPKA, or any part thereof, may be altered during direct synthesis and/or combined using chemical methods with sequences from other proteins, or any part thereof, to produce a variant polypeptide.

Expression Systems

In order to express a biologically active IPKA, the nucleotide sequence encoding IPKA or its functional equivalent, is inserted into an appropriate expression vector, ie, a vector which contains the necessary elements for the transcription and translation of the inserted coding sequence.

Methods which are well known to those skilled in the art can be used to construct expression vectors containing a IPKA coding sequence and appropriate transcriptional or translational controls. These methods include in vitro recombinant DNA techniques, synthetic techniques and in vivo recombination or genetic recombination. Such techniques are described in Sambrook et al (1989) Molecular Cloning, A Laboratory Manual, Cold Spring Harbor Press, Plainview, N.Y. and Ausubel F. M. et al (1989) Current Protocols in Molecular Biology, John Wiley & Sons, New York, N.Y.

A variety of expression vector/host systems may be utilized to contain and express a ipka coding sequence. These include but are not limited to microorganisms such as bacteria transformed with recombinant bacteriophage, plasmid or cosmid DNA expression vectors; yeast transformed with yeast expression vectors; insect cell systems infected with virus expression vectors (eg, baculovirus); plant cell systems transfected with virus expression vectors (eg, cauliflower mosaic virus, CaMV; tobacco mosaic virus, TMV) or transformed with bacterial expression vectors (eg, Ti or pBR322 plasmid); or animal cell systems.

The "control elements" or "regulatory sequences" of these systems vary in their strength and specificities and are those nontranslated regions of the vector, enhancers, promoters, and 3' untranslated regions, which interact with host cellular proteins to carry out transcription and translation. Depending on the vector system and host utilized, any number of suitable transcription and translation elements, including constitutive and inducible promoters, may be used. For example, when cloning in bacterial systems, inducible promoters such as the hybrid lacZ promoter of the Bluescript® phagemid (Stratagene, LaJolla, Calif.) or pSport1 (Gibco BRL) and ptrp-lac hybrids and the like may be used. The baculovirus polyhedrin promoter may be used in insect cells. Promoters or enhancers derived from the genomes of plant cells (eg, heat shock, RUBISCO; and storage protein genes) or from plant viruses (eg, vital promoters or leader sequences) may be cloned into the vector. In mammalian cell systems, promoters from the mammalian genes or from mammalian viruses are most appropriate. If it is necessary to generate a cell line that contains multiple copies of ipka, vectors based on SV40 or EBV may be used with an appropriate selectable marker.

In bacterial systems, a number of expression vectors may be selected depending upon the use intended for IPKA. For example, when large quantities of IPKA are needed for the induction of antibodies, vectors which direct high level expression of fusion proteins that are readily purified may be desirable. Such vectors include, but are not limited to, the multifunctional *E. coli* cloning and expression vectors such as Bluescript® (Stratagene), in which the ipka coding sequence may be ligated into the vector in frame with sequences for the amino-terminal Met and the subsequent 7 residues of β-galactosidase so that a hybrid protein is produced; pIN vectors (Van Heeke & Schuster (1989) J Biol Chem 264:5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems are designed to include heparin, thrombin or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase and PGH may be used. For reviews, see Ausubel et al (supra) and Grant et al (1987) Methods in Enzymology 153:516–544.

In cases where plant expression vectors are used, the expression of a sequence encoding IPKA may be driven by any of a number of promoters. For example, viral promoters such as the 35S and 19S promoters of CaMV (Brisson et al (1984) Nature 310:511–514) may be used alone or in combination with the omega leader sequence from TMV (Takamatsu et al (1987) EMBO J 6:307–311). Alternatively, plant promoters such as the small subunit of RUBISCO (Coruzzi et al (1984) EMBO J 3:1671–1680; Broglie et al (1984) Science 224:838–843); or heat shock promoters (Winter J. and Sinibaldi R. M. (1991) Results Probl Cell Differ 17:85–105) may be used. These constructs can be introduced into plant cells by direct DNA transformation or pathogen-mediated transfection. For reviews of such techniques, see Hobbs S. or Murry L. E. in McGraw Hill *Yearbook of Science and Technology* (1992) McGraw Hill New York, N.Y., pp 191–196 or Weissbach and Weissbach (1988) *Methods for Plant Molecular Biology*, Academic Press, New York, N.Y., pp 421–463.

An alternative expression system which could be used to express ipka is an insect system. In one such system, *Autographa californica* nuclear polyhedrosis virus (AcNPV) is used as a vector to express foreign genes in *Spodoptera frugiperda* cells or in Trichoplusia larvae. The ipka coding sequence may be cloned into a nonessential region of the virus, such as the polyhedrin gene, and placed under control of the polyhedrin promoter. Successful insertion of ipka will render the polyhedrin gene inactive and produce recombinant virus lacking coat protein coat. The recombinant viruses are then used to infect *S. frugiperda* cells or Trichoplusia larvae in which IPKA is expressed (Smith et al (1983) J Virol 46:584; Engelhard E. K. et al (1994) Proc Nat Acad Sci 91:3224–7).

In mammalian host cells, a number of viral-based expression systems may be utilized. In cases where an adenovirus is used as an expression vector, a ipka coding sequence may be ligated into an adenovirus transcription/translation complex consisting of the late promoter and tripartite leader sequence. Insertion in a nonessential E1 or E3 region of the viral genome will result in a viable virus capable of expressing IPKA in infected host cells. (Logan and Shenk (1984) Proc Natl Acad Sci 81:3655–59). In addition, transcription enhancers, such as the rous sarcoma virus (RSV) enhancer, may be used to increase expression in mammalian host cells.

Specific initiation signals may also be required for efficient translation of a ipka sequence. These signals include the ATG initiation codon and adjacent sequences. In cases where ipka, its initiation codon and upstream sequences are inserted into the appropriate expression vector, no additional translational control signals may be needed. However, in cases where only coding sequence, or a portion thereof, is inserted, exogenous transcriptional control signals including the ATG initiation codon must be provided. Furthermore, the initiation codon must be in the correct reading frame to ensure transcription of the entire insert. Exogenous transcriptional elements and initiation codons can be of various origins, both natural and synthetic. The efficiency of expression may be enhanced by the inclusion of enhancers appropriate to the cell system in use (Scharf D. et al (1994) Results Probl Cell Differ 20:125–62; Bittner et al (1987) Methods in Enzymol 153:516–544).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation and acylation. Post-translational processing which cleaves a "prepro" form of the protein may also be important for correct insertion, folding and/or function. Different host cells such as CHO, HeLa, MDCK, 293, WI38, etc have specific cellular machinery and characteristic mechanisms for such post-translational activities and may be chosen to ensure the correct modification and processing of the introduced, foreign protein.

For long-term, high-yield production of recombinant proteins, stable expression is preferred. For example, cell lines which stably express ipka may be transformed using expression vectors which contain viral origins of replication or endogenous expression elements and a selectable marker gene. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clumps of stably transformed cells can be proliferated using tissue culture techniques appropriate to the cell type.

Any number of selection systems may be used to recover transformed cell lines. These include, but are not limited to, the herpes simplex virus thymidine kinase (Wigler M. et al (1977) Cell 11:223–32) and adenine phosphoribosyltransferase (Lowy I. et al (1980) Cell 22:817–23) genes which can be employed in tk- or aprt- cells, respectively. Also, antimetabolite, antibiotic or herbicide resistance can be used as the basis for selection; for example, dhfr which confers resistance to methotrexate (Wigler M. et al (1980) Proc Natl Acad Sci 77:3567–70); npt, which confers resistance to the aminoglycosides neomycin and G-418 (Colbere-Garapin F. et al (1981) J Mol Biol 150:1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman S. C. and R. C. Mulligan (1988) Proc Natl Acad Sci 85:8047–51). Recently, the use of visible markers has gained popularity with such markers as anthocyanins, β glucuronidase and its substrate, GUS, and luciferase and its substrate, luciferin, being widely used not only to identify transformants, but also to quantify the amount of transient or stable protein expression attributable to a specific vector system (Rhodes C. A. et al (1995) Methods Mol Biol 55:121–131).

Identification of Transformants Containing the Polynucleotide Sequence

Although the presence/absence of marker gene expression suggests that the gene of interest is also present, its presence and expression should be confirmed. For example, if the ipka is inserted within a marker gene sequence, recombinant cells containing ipka can be identified by the absence of marker gene function. Alternatively, a marker gene can be placed in tandem with a IPKA sequence under the control of a single promoter. Expression of the marker gene in response to induction or selection usually indicates expression of the tandem ipka as well.

Alternatively, host cells which contain the coding sequence for ipka and express IPKA may be identified by a variety of procedures known to those of skill in the art. These procedures include, but are not limited to, DNA-DNA or DNA-RNA hybridization and protein bioassay or immunoassay techniques which include membrane, solution, or chip based technologies for the detection and/or quantification of the nucleic acid or protein.

The presence of the ipka polynucleotide sequence can be detected by DNA-DNA or DNA-RNA hybridization or amplification using probes, portions or fragments of ipka. Nucleic acid amplification based assays involve the use of oligonucleotides or oligomers based on the ipka sequence to detect transformants containing ipka DNA or RNA. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides which can be used as a probe or amplimer.

A variety of protocols for detecting and measuring the expression of IPKA, using either polyclonal or monoclonal antibodies specific for the protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on IPKA is preferred, but a competitive binding assay may be employed. These and other assays are described, among other places, in Hampton R. et al (1990, Serological Methods, a Laboratory Manual, APS Press, St Paul, Minn.) and Maddox D. E. et al (1983, J Exp Med 158:1211).

A wide variety of labels and conjugation techniques are known by those skilled in the art and can be used in various nucleic acid and amino acid assays. Means for producing labeled hybridization or PCR probes for detecting sequences related to ipka include oligolabeling, nick translation, end-labeling or PCR amplification using a labeled nucleotide. Alternatively, the ipka sequence, or any portion of it, may be cloned into a vector for the production of an mRNA probe. Such vectors are known in the art, are commercially available, and may be used to synthesize RNA probes in vitro by addition of an appropriate RNA polymerase such as T7, T3 or SP6 and labeled nucleotides.

A number of companies such as Pharmacia Biotech (Piscataway, N.J.), Promega (Madison, Wis.), and US Biochemical Corp (Cleveland, Ohio) supply commercial kits and protocols for these procedures. Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. Nos. 3,817,837; 3,850,752; 3,939,350; 3,996,345; 4,277,437; 4,275,149 and 4,366,241. Also, recombinant immunoglobulins may be produced as shown in U.S. Pat. No. 4,816,567 incorporated herein by reference.

Purification of IPKA

Host cells transformed with a ipka nucleotide sequence may be cultured under conditions suitable for the expression and recovery of the encoded protein from cell culture. The protein produced by a recombinant cell may be secreted or contained intracellularly depending on the sequence and/or the vector used. As will be understood by those of skill in the art, expression vectors containing ipka can be designed with signal sequences which direct secretion of IPKA through a prokaryotic or eukaryotic cell membrane. Other recombinant constructions may join ipka to nucleotide sequence encoding a polypeptide domain which will facilitate purification of soluble proteins (Kroll D. J. et al (1993) DNA Cell Biol 12:441–53; cf discussion of vectors infra containing fusion proteins).

IPKA may also be expressed as a recombinant protein with one or more additional polypeptide domains added to facilitate protein purification. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp, Seattle, Wash.). The inclusion of a cleavable linker sequences such as Factor XA or enterokinase (Invitrogen, San Diego, Calif.) between the purification domain and IPKA is useful to facilitate purification. One such expression vector provides for expression of a fusion protein compromising an IPKA and contains nucleic acid encoding 6 histidine residues followed by thioredoxin and an enterokinase cleavage site. The histidine residues facilitate purification on IMIAC (immobilized metal ion affinity chromotography as described in Porath et al (1992) Protein Expression and Purification 3: 263–281) while the enterokinase cleavage site provides a means for purifying the chemokine from the fusion protein.

In addition to recombinant production, fragments of IPKA may be produced by direct peptide synthesis using solid-phase techniques (cf Stewart et al (1969) Solid-Phase Peptide Synthesis, W. H. Freeman Co, San Francisco; Merrifield J. (1963) J Am Chem Soc 85:2149–2154). In vitro protein synthesis may be performed using manual techniques or by automation. Automated synthesis may be achieved, for example, using Applied Biosystems 431A Peptide Synthesizer (Perkin Elmer, Foster City, Calif.) in accordance with the instructions provided by the manufacturer. Various fragments of IPKA may be chemically synthesized separately and combined using chemical methods to produce the full length molecule.

Uses of IPKA

The rationale for use of the nucleotide and polypeptide sequences disclosed herein is based in part on the chemical and structural homology among the novel human IPKA disclosed herein, the avian PKI (GI 632652; Marchetto and Henry, supra), and human PKI alpha (GI 243494; Olsen and Uhler, supra).

Scala S. et al (1995; supra) showed that the selective PKA inhibitor 8-Cl-cAMP decreases MDR1 expression in multidrug-resistant human breast cancer cells. The authors suggest that the selective inhibition of PKA might allow successful management of breast cancer with standard cytotoxic chemotherapeutic regimens. Therefore, IPKA or an IPKA derived molecule may provide inhibition of PKA thereby prolonging the effectiveness of standard chemotherapy.

Bold et al (1994; Surgery 116: 189–195) experimented with PKA inhibitors on colon cancer cells. They found that gastrin and 8-Br-cAMP act to inhibit the growth of HCT116 cells by PKA inhibition. Wen Wet al (1995; supra) found that PKI alpha plays an important role in the inhibition of the PKA C subunit activity required for cell cycle progression. Therefore, IPKA or an IPKA derived molecule may inhibit cancer cell growth by interfering with the cell cycle.

In those disorders where PKA activity is desirable, cells could be transfected with antisense sequences of ipka or provided with inhibitors of IPKA. Such disorders include asthma, cystic fibrosis, systemic lupus erythematosus, and those that affect memory or learning, such as Alzheimer's disease.

IPKA Antibodies

IPKA-specific antibodies are useful for the diagnosis of conditions and diseases associated with expression of IPKA. IPKA for antibody induction does not require biological activity; however, the protein fragment, or oligopeptide must be antigenic. Peptides used to induce specific antibodies may have an amine acid sequence consisting of at least five amino acids, preferably at least 10 amino acids. They should mimic a portion of the amino acid sequence of the natural protein and may contain the entire amino acid sequence of a small, naturally occurring molecule. Short stretches of IPKA amino acids may be fused with those of another protein such as keyhole limpet hemocyanin and antibody produced against the chimeric molecule. Procedures well known in the art can be used for the production of antibodies to IPKA. Such antibodies include, but are not limited to, polyclonal, monoclonal, chimetic, single chain, Fab fragments and fragments produced by a Fab expression library. Neutralizing antibodies, ie, those which inhibit dimer formation, are especially preferred for diagnostics and therapeutics.

For the production of antibodies, various hosts including goats, rabbits, rats, mice, etc. may be immunized by injection with IPKA or any portion, fragment or oligopeptide which retains immunogenic properties. Depending on the host species, various adjuvants may be used to increase immunological response. Such adjuvants include but are not limited to Freund's, mineral gels such as aluminum hydroxide, and surface active substances such as lysolecithin, pluronic polyols, polyanions, peptides, oil emulsions, keyhole limpet hemocyanin, and dinitrophenol. BCG (bacilli Calmette-Guerin) and *Corynebacterium parvum* are potentially useful human adjuvants.

Monoclonal antibodies to IPKA may be prepared using any technique which provides for the production of antibody molecules by continuous cell lines in culture. These include but are not limited to the hybridoma technique originally described by Koehler and Milstein (1975 Nature 256:495–497), the human B-cell hybridoma technique (Kosbor et al (1983) Immunol Today 4:72; Cote et al (1983) Proc Natl Acad Sci 80:2026–2030) and the EBV-hybridoma technique (Cole et al (1985) *Monoclonal Antibodies and Cancer Therapy*, Alan R. Liss Inc, New York, N.Y., pp 77–96).

In addition, techniques developed for the production of "chimeric antibodies", the splicing of mouse antibody genes to human antibody genes to obtain a molecule with appropriate antigen specificity and biological activity can be used (Morrison et al (1984) Proc Natl Acad Sci 81:6851–6855; Neuberger et al (1984) Nature 312:604–608; Takeda et al (1985) Nature 314:452–454). Alternatively, techniques described for the production of single chain antibodies (U.S. Pat. No. 4,946,778) can be adapted to produce IPKA-specific single chain antibodies.

Antibodies may also be produced by inducing in vivo production in the lymphocyte population or by screening recombinant immunoglobulin libraries or panels of highly specific binding reagents as disclosed in Orlandi et al (1989, Proc Natl Acad Sci 86: 3833–3837), and Winter G. and Milstein C. (1991; Nature 349:293–299).

Antibody fragments which contain specific binding sites for IPKA may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse W. D. et al (1989) Science 256:1275–1281).

A variety of protocols for competitive binding or immunoradiometric assays using either polyclonal or monoclonal antibodies with established specificities are well known in the art. Such immunoassays typically involve the formation of complexes between IPKA and its specific antibody and the measurement of complex formation. A two-site, monoclonal-based immunoassay utilizing monoclonal antibodies reactive to two noninterfering epitopes on a specific IPKA protein is preferred, but a competitive binding assay may also be employed. These assays are described in Maddox D. E. et al (1983, J Exp Med 158:1211).

Diagnostic Assays Using IPKA Specific Antibodies

Particular IPKA antibodies are useful for the diagnosis of conditions or diseases characterized by expression of IPKA or in assays to monitor patients being treated with IPKA, agonists or inhibitors. Diagnostic assays for IPKA include methods utilizing the antibody and a label to detect IPKA in human body fluids or extracts of cells or tissues. The polypeptides and antibodies of the present invention may be used with or without modification. Frequently, the polypeptides and antibodies will be labeled by joining them, either covalently or noncovalently, with a reporter molecule. A wide variety of reporter molecules are known, several of which were described above.

A variety of protocols for measuring IPKA, using either polyclonal or monoclonal antibodies specific for the respective protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on IPKA is preferred, but a competitive binding assay may be employed. These assays are described, among other places, in Maddox, D. E. et al (1983, J Exp Med 158:1211).

In order to provide a basis for diagnosis, normal or standard values for IPKA expression must be established. This is accomplished by combining body fluids or cell extracts taken from normal subjects, either animal or human, with antibody to IPKA under conditions suitable for complex formation which are well known in the art. The amount of standard complex formation may be quantified by comparing various artificial membranes containing known quantities of IPKA with both control and disease samples from biopsied tissues. Then, standard values obtained from normal samples may be compared with values obtained from samples from subjects potentially affected by disease. Deviation between standard and subject values establishes the presence of disease state.

Drug Screening

IPKA, its catalytic or immunogenic fragments or oligopeptides thereof, can be used for screening therapeutic compounds in any of a variety of drug screening techniques. The fragment employed in such a test may be free in solution, affixed to a solid support, borne on a cell surface, or located intracellulary. The formation of binding complexes, between IPKA and the agent being tested, may be measured.

Another technique for drug screening which provides for high throughput screening of compounds having suitable binding affinity to the IPKA is described in detail in "Determination of Amino Acid Sequence Antigenicity" by Geysen H. N., WO Application 84/03564, published on Sep. 13, 1984, and incorporated herein by reference. In summary, large numbers of different small peptide test compounds are synthesized on a solid substrate, such as plastic pins or some other surface. The peptide test compounds are reacted with fragments of IPKA and washed. Bound IPKA is then detected by methods well known in the art. Purified IPKA can also be coated directly onto plates for use in the aforementioned drug screening techniques. Alternatively, non-neutralizing antibodies can be used to capture the peptide and immobilize it on a solid support.

This invention also contemplates the use of competitive drug screening assays in which neutralizing antibodies capable of binding IPKA specifically compete with a test compound for binding IPKA. In this manner, the antibodies can be used to detect the presence of any peptide which shares one or more antigenic determinants with IPKA.

Uses of the Polynucleotide Encoding IPKA

A polynucleotide, ipka, or any part thereof, may be used for diagnostic and/or therapeutic purposes. For diagnostic purposes, the ipka of this invention may be used to detect and quantitate gene expression in biopsied tissues in which expression of IPKA may be implicated. The diagnostic assay is useful to distinguish between absence, presence, and excess expression of ipka and to monitor regulation of ipka levels during therapeutic intervention. Included in the scope of the invention are oligonucleotide sequences, antisense RNA and DNA molecules, and PNAs.

Another aspect of the subject invention is to provide for hybridization or PCR probes which are capable of detecting polynucleotide sequences, including genomic sequences, encoding IPKA or closely related molecules. The specificity of the probe, whether it is made from a highly specific region, eg, 10 unique nucleotides in the 5' regulatory region, or a less specific region, eg, especially in the 3' region, and the stringency of the hybridization or amplification (maximal, high, intermediate or low) will determine whether the probe identifies only naturally occurring ipka, alleles or related sequences.

It will be appreciated by those skilled in the art that as a result of the degeneracy of the genetic code, a multitude of IPKA-encoding nucleotide sequences, some bearing minimal homology to the nucleotide sequences of any known and naturally occurring gene may be produced. The invention has specifically contemplated each and every possible variation of nucleotide sequence that could be made by selecting combinations based on possible codon choices. These combinations are made in accordance with the standard triplet genetic code as applied to the nucleotide sequence of naturally occurring IPKA, and all such variations are to be considered as being specifically disclosed.

Probes may also be used for the detection of related inhibitor encoding sequences and should preferably contain at least 50% of the nucleotides from any of these IPKA encoding sequences. The hybridization probes of the subject invention may be derived from the nucleotide sequence of the SEQ ID NO:1 or from genomic sequence including promoter, enhancer elements and introns of the naturally occurring ipka. Hybridization probes may be labeled by a variety of reporter groups, including radionuolides such as 32P or 35S, or enzymatic labels such as alkaline phosphatase coupled to the probe via avidin/biotin coupling systems, and the like.

Other means for producing specific hybridization probes for ipka DNAs include the cloning of nucleic acid sequences encoding IPKA or IPKA derivatives into vectors for the production of mRNA probes. Such vectors are known in the art and are commercially available and may be used to synthesize RNA probes in vitro by means of the addition of the appropriate RNA polymerase as T7 or SP6 RNA polymerase and the appropriate radioactively labeled nucleotides.

Diagnostics

Polynucleotide sequences encoding IPKA may be used for the diagnosis of conditions or diseases with which the expression of IPKA is associated. For example, polynucleotide sequences encoding IPKA may be used in hybridization or PCR assays of fluids or tissues from biopsies to detect ipka expression. The form of such qualitative or quantitative methods may include Southern or northern analysis, dot blot or other membrane-based technologies; PCR technologies; dip stick, pin, chip and ELISA technologies. All of these techniques are well known in the art and are the basis of many commercially available diagnostic kits.

The ipka nucleotide sequences disclosed herein provide the basis for assays that detect activation or induction associated with inflammation or disease. The ipka nucleotide sequence may be labeled by methods known in the art and added to a fluid or tissue sample from a patient under conditions suitable for the formation of hybridization complexes. After an incubation period, the sample is washed with a compatible fluid which optionally contains a dye (or other label requiring a developer) if the nucleotide has been labeled with an enzyme. After the compatible fluid is rinsed off, the dye is quantitated and compared with a standard. If the amount of dye in the biopsied or extracted sample is significantly elevated over that of a comparable control sample, the nucleotide sequence has hybridized with nucleotide sequences in the sample, and the presence of elevated levels of ipka nucleotide sequences in the sample indicates the presence of the associated inflammation and/or disease.

Such assays may also be used to evaluate the efficacy of a particular therapeutic treatment regime in animal studies, in clinical trials, or in monitoring the treatment of an individual patient. In order to provide a basis for the diagnosis of disease, a normal or standard profile for ipka expression must be established. This is accomplished by combining body fluids or cell extracts taken from normal subjects, either animal or human, with ipka, or a portion thereof, under conditions suitable for hybridization or amplification. Standard hybridization may be quantified by comparing the values obtained for normal subjects with a dilution series of ipka run in the same experiment where a known amount of purified ipka is used. Standard values obtained from normal samples may be compared with values obtained from samples from patients affected by ipka-associated diseases. Deviation between standard and subject values establishes the presence of disease.

Once disease is established, a therapeutic agent is administered and a treatment profile is generated. Such assays may be repeated on a regular basis to evaluate whether the values in the profile progress toward or return to the normal or standard pattern. Successive treatment profiles may be used to show the efficacy of treatment over a period of several days or several months.

PCR as described in U.S. Pat. Nos. 4,683,195 and 4,965,188 provides additional uses for oligonucleotides based upon the ipka sequence. Such oligomers are generally chemically synthesized, but they may be generated enzymatically or produced from a recombinant source. Oligomers generally comprise two nucleotide sequences, one with sense orientation (5'→3') and one with antisense (3'←5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Additionally, methods to quantitate the expression of a particular molecule include radiolabeling (Melby P. C. et al 1993 J Immunol Methods 159:235–44) or biotinylating (Duplaa C. et al 1993 Anal Biochem 229–36) nucleotides, coamplification of a control nucleic acid, and standard curves onto which the experimental results are interpolated. Quantitation of multiple samples may be speeded up by running the assay in an ELISA format where the oligomer of interest is presented in various dilutions and a spectrophotometric or colorimetric response gives rapid quantitation. For example, the presence of ipka in extracts of biopsied tissues may indicate the onset of cancer. A definitive diagnosis of this type may allow health professionals to begin aggressive treatment and prevent further worsening of the condition. Similarly, further assays can be used to monitor the progress of a patient during treatment. Furthermore, the nucleotide sequences disclosed herein may be used in molecular biology techniques that have not yet been developed, provided the new techniques rely on properties of nucleotide sequences that are currently known such as the triplet genetic code, specific base pair interactions, and the like.

Therapeutics

Based upon its homology to the avian PKI gene and its expression profile the ipka polynucleotide disclosed herein may be useful in the treatment of conditions such as prostate, colon, and breast cancers, cystic fibrosis, and autoimmune diseases such as, asthma and systemic lupus erythematosus.

Expression vectors derived from retroviruses, adenovirus, herpes or vaccinia viruses, or from various bacterial plasmids, may be used for delivery of nucleotide sequences to the targeted organ, tissue or cell population. Methods which are well known to those skilled in the art can be used to construct recombinant vectors which will express antisense ipka. See, for example, the techniques described in Sambrook et al (supra) and Ausubel et al (supra).

The polynucleotides comprising full length cDNA sequence and/or its regulatory elements enable researchers to use ipka as an investigative tool in sense (Youssoufian H. and H. F. Lodish 1993 Mol Cell Biol 13:98–104) or antisense (Eguchi et al (1991) Annu Rev Biochem 60:631–652) regulation of gene function. Such technology is now well known in the art, and sense or antisense oligomers, or larger fragments, can be designed from various locations along the coding or control regions.

Genes encoding IPKA can be turned off by transfecting a cell or tissue with expression vectors which express high levels of a desired ipka fragment. Such constructs can flood cells with untranslatable sense or antisense sequences. Even in the absence of integration into the DNA, such vectors may continue to transcribe RNA molecules until all copies are disabled by endogenous nucleases. Transient expression may last for a month or more with a non-replicating vector (Mettler I, personal communication) and even longer if appropriate replication elements are part of the vector system.

As mentioned above, modifications of gene expression can be obtained by designing antisense molecules, DNA, RNA or PNA, to the control regions of ipka, ie, the promoters, enhancers, and introns. Oligonucleotides derived from the transcription initiation site, eg, between −10 and +10 regions of the leader sequence, are preferred. The antisense molecules may also be designed to block translation of mRNA by preventing the transcript from binding to ribosomes. Similarly, inhibition can be achieved using "triple helix" base-pairing methodology. Triple helix pairing compromises the ability of the double helix to open sufficiently for the binding of polymerases, transcription factors, or regulatory molecules. Recent therapeutic advances using triplex DNA were reviewed by Gee J. E. et al (In: Huber B. E. and B. I. Carr (1994) *Molecular and Immunologic Approaches*, Futura Publishing Co, Mt Kisco, N.Y.).

Ribozymes are enzymatic RNA molecules capable of catalyzing the specific cleavage of RNA. The mechanism of ribozyme action involves sequence-specific hybridization of the ribozyme molecule to complementary target RNA, followed by endonucleolytic cleavage. Within the scope of the invention are engineered hammerhead motif ribozyme molecules that can specifically and efficiently catalyze endonucleolytic cleavage of ipka.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of RNA molecules. These include techniques for chemically synthesizing oligonucleotides such as solid phase phosphoramidite chemical synthesis. Alternatively, RNA molecules may be generated by in vitro and in vivo transcription of DNA sequences encoding IPKA. Such DNA sequences may be incorporated into a wide variety of vectors with suitable RNA polymerase promoters such as T7 or SP6. Alternatively, antisense cDNA constructs that synthesize antisense RNA constitutively or inducibly can be introduced into cell lines, cells or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine and wybutosine as well as acetyl-, methyl-, thio- and similarly modified forms of adenine, cytidine, guanine, thymine, and uridine which are not as easily recognized by endogenous endonucleases.

Methods for introducing vectors into cells or tissues include those methods discussed infra and which are equally suitable for in vivo, in vitro and ex vivo therapy. For ex vivo therapy, vectors are introduced into stem cells taken from the patient and clonally propagated for autologous transplant back into that same patient is presented in U.S. Pat. Nos. 5,399,493 and 5,437,994, disclosed herein by reference. Delivery by transfection and by liposome are quite well known in the art.

Furthermore, the nucleotide sequences for ipka disclosed herein may be used in molecular biology techniques that have not yet been developed, provided the new techniques rely on properties of nucleotide sequences that are currently known, including but not limited to such properties as the triplet genetic code and specific base pair interactions.

Detection and Mapping of Related Polynucleotide Sequences

The nucleic acid sequence for ipka can also be used to generate hybridization probes for mapping the naturally occurring genomic sequence. The sequence may be mapped to a particular chromosome or to a specific region of the chromosome using well known techniques. These include in situ hybridization to chromosomal spreads, flow-sorted chromosomal preparations, or artificial chromosome constructions such as yeast artificial chromosomes, bacterial artificial chromosomes, bacterial P1 constructions or single chromosome cDNA libraries as reviewed in Price C. M. (1993; Blood Rev 7:127–34) and Trask B. J. (1991; Trends Genet 7:149–54).

The technique of fluorescent in situ hybridization of chromosome spreads has been described, among other places, in Verma et al (1988) Human Chromosomes: A Manual of Basic Techniques, Pergamon Press, New York, N.Y. Fluorescent in situ hybridization of chromosomal preparations and other physical chromosome mapping techniques may be correlated with additional genetic map data. Examples of genetic map data can be found in the 1994 Genome Issue of Science (265:1981f). Correlation between the location of a ipka on a physical chromosomal map and a specific disease (or predisposition to a specific disease) may help delimit the region of DNA associated with that genetic disease. The nucleotide sequences of the subject invention may be used to detect differences in gene sequences between normal, carrier or affected individuals.

In situ hybridization of chromosomal preparations and physical mapping techniques such as linkage analysis using established chromosomal markers are invaluable in extending genetic maps. A recent example of an STS based map of the human genome was recently published by the Whitehead-MIT Center for Genomic Research (Hudson T. J. et al (1995) Science 270:1945–1954). Often the placement of a gene on the chromosome of another mammalian species such as mouse (Whitehead Institute/MIT Center for Genome Research, Genetic Map of the Mouse, Database Release 10, Apr. 28, 1995) may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once a disease or syndrome, such as ataxia telangiectasia (AT), has been crudely localized by genetic linkage to a particular genomic region, for example, AT to 11q22–23 (Gatti et al (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier or affected individuals.

Pharmaceutical Compositions

The present invention comprises pharmaceutical compositions which may comprise nucleotides, proteins, antibodies, antagonists, or inhibitors, alone or in combination with at least one other agent, such as stabilizing compound, which may be administered in any sterile, biocompatible pharmaceutical carrier, including, but not limited to, saline, buffered saline, dextrose, and water. Any of these molecules can be administered to a patient alone, or in combination with other agents, drugs or hormones, in pharmaceutical compositions where it is mixed with excipient(s) or pharmaceutically acceptable carriers. In one embodiment of the present invention, the pharmaceutically acceptable carrier is pharmaceutically inert.

Administration of Pharmaceutical Compositions

Administration of pharmaceutical compositions is accomplished orally or parenterally. Methods of parenteral delivery include topical, intra-arterial (directly to the tumor), intramuscular, subcutaneous, intramedullary, intrathecal, intraventricular, intravenous, intraperitoneal, or intranasal administration. In addition to the active ingredients, these pharmaceutical compositions may contain suitable pharmaceutically acceptable carriers comprising excipients and auxiliaries which facilitate processing of the active compounds into preparations which can be used pharmaceutically. Further details on techniques for formulation and administration may be found in the latest edition of "Remington's Pharmaceutical Sciences" (Maack Publishing Co, Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, or other plants; cellulose such as methyl cellulose, hydroxypropylmethylcellulose, or sodium carboxymethylcellulose; and gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, ie, dosage.

Pharmaceutical preparations which can be used orally include push-fit capsules made of gelatin, as well as soft, sealed capsules made of gelatin and a coating such as glycerol or sorbitol. Push-fit capsules can contain active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Pharmaceutical formulations for parenteral administration include aqueous solutions of active compounds. For injection, the pharmaceutical compositions of the invention may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

Manufacture and Storage

The pharmaceutical compositions of the present invention may be manufactured in a manner that known in the art, eg, by means of conventional mixing, dissolving, granulating, dragee-making, levigating, emulsifying, encapsulating, entrapping or lyophilizing processes.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM–50 mM histidine, 0.1%–2% sucrose, 2%–7% mannitol at a pH range of 4.5 to 5.5 that is combined with buffer prior to use.

After pharmaceutical compositions comprising a compound of the invention formulated in an acceptable carrier have been prepared, they can be placed in an appropriate container and labeled for treatment of an indicated condition. For administration of IPKA, such labeling would include amount, frequency and method of administration.

Therapeutically Effective Dose

Pharmaceutical compositions suitable for use in the present invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, eg, of neoplastic cells, or in animal models, usually mice, rabbits, dogs, or pigs. The animal model is also used to achieve a desirable concentration range and route of administration. Such information can then be used to determine useful doses and routes for administration in humans.

A therapeutically effective dose refers to that amount of protein or its antibodies, antagonists, or inhibitors which ameliorate the symptoms or condition. Therapeutic efficacy and toxicity of such compounds can be determined by standard pharmaceutical procedures in cell cultures or experimental animals, eg, ED50 (the dose therapeutically effective in 50% of the population) and LD50 (the dose lethal to 50% of the population). The dose ratio between therapeutic and toxic effects is the therapeutic index, and it can be expressed as the ratio, ED50/LD50. Pharmaceutical compositions which exhibit large therapeutic indices are preferred. The data obtained from cell culture assays and animal studies is used in formulating a range of dosage for human use. The dosage of such compounds lies preferably within a range of circulating concentrations that include the ED50 with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors which may be taken into account include the severity of the disease state, eg, tumor size and location; age, weight and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature. See U.S. Pat. Nos. 4,657,760; 5,206,344; or 5,225,212. Those skilled in the art will employ different formulations for nucleotides than for proteins or their inhibitors. Similarly, delivery of polynucleotides or polypeptides will be specific to particular cells, conditions, locations, etc.

It is contemplated, for example, that IPKA or an IPKA derivative can be delivered in a suitable formulation to prevent the induction of MDR in cancer cells. Such treatment would prevent the onset of drug resistant cancer cells and allow eradication of the cancer. Similarly, administration of agonists should also improve the activity or lifespan of this protein and lessen the onset and progression of various cancers.

The examples below are provided to illustrate the subject invention and are not included for the purpose of limiting the invention.

EXAMPLES

I cDNA Library Construction

The CERVNOT01 cDNA library was constructed from normal cervix tissue obtained from a 35-year-old Caucasian female (specimen #0210A; Mayo Clinic, Rochester, Minn.) by vaginal hysterectomy. The patient was observed initially with abdominal pain. She had previously been treated with dilation & curettage of the uterus. The patient also had undergone cholecystectomy and tonsillectomy with adenoidectomy. There was also a history of atherosclerosis. The patient was taking Prozac® (fluoxetine hydrochoride; Dista Products and Eli Lilly and Company, Indianapolis, Ind.) and Synthroid® (Levothyroxine Sodium; Knoll Pharmaceutical Company, Mount Olive, N.J.) prior to surgery.

The frozen tissue was homogenized and lysed using a Brinkmann Homogenizer Polytron-PT 3000 (Brinkmann Instruments, Inc. Westbury, N.Y.) in guanidinium isothiocyanate solution. The lysates were extracted once with acid phenol at pH 4.0 per Stratagene's RNA isolation protocol (Stratagene Inc, San Diego, Calif.). The RNA was extracted twice with an equal volume of acid phenol, reprecipitated using 0.3M sodium acetate and 2.5 volumes of ethanol, resuspended in DEPC-treated water and DNase treated for 25 rain at 37° C. mRNAs were isolated using the Qiagen Oligotex kit (QIAGEN Inc,) and used to construct the cDNA library.

The mRNA was handled according to the recommended protocols in the SuperScript Plasmid System for cDNA Synthesis and Plasmid Cloning (Cat. #18248-013; Gibco/BRL). cDNAs were fractionated on a Sepharose CL4B column (Cat. #275105-01; Pharmacia), and those cDNAs exceeding 400 bp were ligated into pSport I. The plasmid pSport I was subsequently transformed into DH5a™ competent cells (Cat. #18258-012; Gibco/BRL).

II Isolation and Sequencing of cDNA Clones

Plasmid DNA was released from the cells and purified using the REAL Prep 96 Plasmid Kit for Rapid Extraction Alkaline Lysis Plasmid Minipreps (Catalog #26173; QIAGEN, Inc). This kit enables the simultaneous purification of 96 samples in a 96-well block using multi-channel reagent dispensers. The recommended protocol was employed except for the following changes: 1) the bacteria were cultured in 1 ml of sterile Terrific Broth (Catalog #22711, LIFE TECHNOLOGIES™) with carbenicillin at 25 mg/L and glycerol at 0.4%; 2) after inoculation, the cultures were incubated for 19 hours and at the end of incubation, the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

The cDNAs were sequenced by the method of Sanger F. and A. R. Coulson (1975; J Mol Biol 94:441f), using a Hamilton Micro Lab 2200 (Hamilton, Reno, Nev.) in combination with Peltier Thermal Cyclers (PTC200 from MJ Research, Watertown, Mass.) and Applied Biosystems 377 DNA Sequencing Systems; and the reading frame was determined.

III Homology Searching of cDNA Clones and Their Deduced Proteins

Each cDNA was compared to sequences in GenBank using a search algorithm developed by Applied Biosystems and incorporated into the INHERIT™ 670 Sequence Analysis System. In this algorithm, Pattern Specification Language (TRW Inc, Los Angeles, Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT™ 670 Sequence Analysis System in a way similar to that used in DNA sequence homologies. Pattern Specification Language and parameter windows were used to search protein databases for sequences containing regions of homology which were scored with an initial value. Dot-matrix homology plots were examined to distinguish regions of significant homology from chance matches.

BLAST, which stands for Basic Local Alignment Search Tool (Altschul S. F. (1993) J Mol Evol 36:290–300; Altschul, S. F. et al (1990) J Mol Biol 215:403–10), was used to search for local sequence alignments. BLAST produces alignments of both nucleotide and amine acid sequences to determine sequence similarity. Because of the local nature of the alignments, BLAST is especially useful in determining exact matches or in identifying homologs. BLAST is useful for matches which do not contain gaps. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

IV Northern Analysis

Northern analysis is a laboratory technique used to detect the presence of a transcript of a gene which involves the hybridization of a labelled nucleotide sequence to a membrane on which RNAs from a particular cell type or tissue have been bound (Sambrook et al. supra). Northern analysis can be used to detect the presence of a transcript of the gene using a labelled nucleotide sequence.

Analogous computer techniques using BLAST (Altschul SF 1993 and 1990, supra) are used to search for identical or related molecules in nucleotide databases such as the GenBank or the LIFESEQ™ database (Incyte, Palo Alto, Calif.). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\% \text{ sequence identity} \times \% \text{ maximum BLAST score}}{100}$$

and it takes into acccount both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

V Extension of IPKA to Full Length or to Recover Regulatory Elements

The nucleic acid sequence of full length IPKA (SEQ ID NO:1) is used to design oligonucleotide primers for extending a partial nucleotide sequence to full length or for obtaining 5' sequences from genomic libraries. One primer is synthesized to initiate extension in the antisense direction (XLR) and the other is synthesized to extend sequence in the sense direction (XLF). Primers allow the extension of the known IPKA sequence "outward" generating amplicons containing new, unknown nucleotide sequence for the region of interest (U.S. patent application Ser. No. 08/487,112, filed Jun. 7, 1995, specifically incorporated by reference). The initial primers are designed from the cDNA using OLIGO® 4.06 Primer Analysis Software (National Biosciences), or another appropriate program, to be 22–30 nucleotides in length, to have a GC content of 50% or more, and to anneal to the target sequence at temperatures about 68°–72° C. Any stretch of nucleotides which would result in hairpin structures and primer-primer dimerizations is avoided.

The original, selected cDNA libraries, or a human genomic library are used to extend the sequence; the latter is most useful to obtain 5' upstream regions. If more extension is necessary or desired, additional sets of primers are designed to further extend the known region.

By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier Thermal Cycler (PTC200; MJ Research, Watertown, Mass.) and the following parameters:

| | |
|---|---|
| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4–6 for 15 additional cycles |
| Step 8 | 94° C. for 15 sec |
| Step 9 | 65° C. for 1 min |
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 µl aliquot of the reaction mixture is analyzed by electrophoresis on a low concentration (about 0.6–0.8%) agarose mini-gel to determine which reactions were successful in extending the sequence. Bands thought to contain the largest products were selected and cut out of the gel. Further purification involves using a commercial gel extraction method such as QIAQuick™ (QIAGEN Inc). After recovery of the DNA, Klenow enzyme was used to trim single-stranded, nucleotide overhangs creating blunt ends which facilitate religation and cloning.

After ethanol precipitation, the products are redissolved in 13 µl of ligation buffer, 1 µl T4-DNA ligase (15 units) and 1 µl T4 polynucleotide kinase are added, and the mixture is incubated at room temperature for 2–3 hours or overnight at 16° C. Competent E. coli cells (in 40 µl of appropriate media) are transformed with 3 µl of ligation mixture and cultured in 80 µl of SOC medium (Sambrook J. et al, supra). After incubation for one hour at 37° C., the whole transformation mixture is plated on Luria Bertani (LB)-agar (Sambrook J. et al, supra) containing 2xCarb. The following day, several colonies are randomly picked from each plate and cultured in 150 µl of liquid LB/2xCarb medium placed in an individual well of an appropriate, commercially-available, sterile 96-well microtiter plate. The following day, 5 µl of each overnight culture is transferred into a non-sterile 96-well plate and after dilution 1:10 with water, 5 µl of each sample is transferred into a PCR array.

For PCR amplification, 18 µl of concentrated PCR reaction mix (3.3x) containing 4 units of rTth DNA polymerase, a vector primer and one or both of the gene specific primers used for the extension reaction are added to each well. Amplification is performed using the following conditions:

| | |
|---|---|
| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 41° C. (and holding) |

Aliquots of the PCR reactions are run on agarose gels together with molecular weight markers. The sizes of the PCR products are compared to the original partial cDNAs, and appropriate clones are selected, ligated into plasmid and sequenced.

VI Labeling and Use of Hybridization Probes

Hybridization probes derived from SEQ ID NO:1 are employed to screen cDNAs, genomic DNAs or mRNAs. Although the labeling of oligonucleotides, consisting of about 20 base-pairs, is specifically described, essentially the same procedure is used with larger cDNA fragments. Oligonucleotides are designed using state-of-the-art software such as OLIGO 4.06 (National Biosciences), labeled by combining 50 pmol of each oligomer and 250 mCi of $[\gamma-^{32}P]$ adenosine triphosphate (Amersham, Chicago, Ill.) and T4 polynucleotide kinase (DuPont NEN®, Boston, Mass.). The labeled oligonucleotides are purified with Sephadex G-25 super fine resin column (Pharmacia). A portion containing $10^7$ counts per minute of each of the sense and antisense oligonucleotides is used in a typical membrane based hybridization analysis of human genomic DNA digested with one of the following endonucleases (Ase I, Bgl II, Eco RI, Pst I, Xba 1, or Pvu II; DuPont NEN®).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1 x saline sodium citrate and 0.5% sodium dodecyl sulfate. After XOMAT AR™ film (Kodak, Rochester, N.Y.) is exposed to the blots in a Phosphoimager cassette (Molecular Dynamics, Sunnyvale, Calif.) for several hours, hybridization patterns are compared visually.

VII Antisense Molecules

The ipka sequence, or any part thereof, is used to inhibit in vivo or in vitro expression of naturally occurring ipka.

Although use of antisense oligonucleotides, comprising about 20 base-pairs, is specifically described, essentially the same procedure is used with larger cDNA fragments. An oligonucleotide based on the coding sequence of IPKA as shown in FIG. 1 is used to inhibit expression of naturally occurring IPKA. The complementary oligonucleotide is designed from the most unique 5' sequence as shown in FIG. 1 and used either to inhibit transcription by preventing promoter binding to the upstream nontranslated sequence or translation of an ipka transcript by preventing the ribosome from binding. Using an appropriate portion of the leader and 5' sequence of SEQ ID NO:1, an effective antisense oligonucleotide includes any 15–20 nucleotides spanning the region which translates into the signal or early coding sequence of the polypeptide as shown in FIG. 1.

VIII Expression of IPKA

Expression of the IPKA is accomplished by subcloning the cDNAs into appropriate vectors and transfecting the vectors into host cells. In this case, the cloning vector, pSport, previously used for the generation of the cDNA library is used to express IPKA in *E. coli*. Upstream of the cloning site, this vector contains a promoter for β-galactosidase, followed by sequence containing the amino-terminal Met and the subsequent 7 residues of β-galactosidase. Immediately following these eight residues is a bacteriophage promoter useful for transcription and a linker containing a number of unique restriction sites.

Induction of an isolated, transfected bacterial strain with IPTG using standard methods produces a fusion protein which consists of the first seven residues of β-galactosidase, about 5 to 15 residues of linker, and the full length IPKA. The signal sequence directs the secretion of IPKA into the bacterial growth media which can be used directly in the following assay for activity.

IX IPKA Activity

IPKA is assayed as to its effects in vitro on PKA activity. PKA activity is found by measuring the transfer of radioactivity from [gamma-$^{32}$P]-ATP to a synthetic substrate, such as the heptapeptide LRRASLG in the presence of cAMP (Roskoski R. Meth Enzymol 99: 3–6). IPKA is added to the reaction mixture prior to the addition of substrate. The effect on PKA activity is measured at many dosages of IPKA and compared to a negative (without IPKA) control.

X Production of IPKA Specific Antibodies

Figure 5:
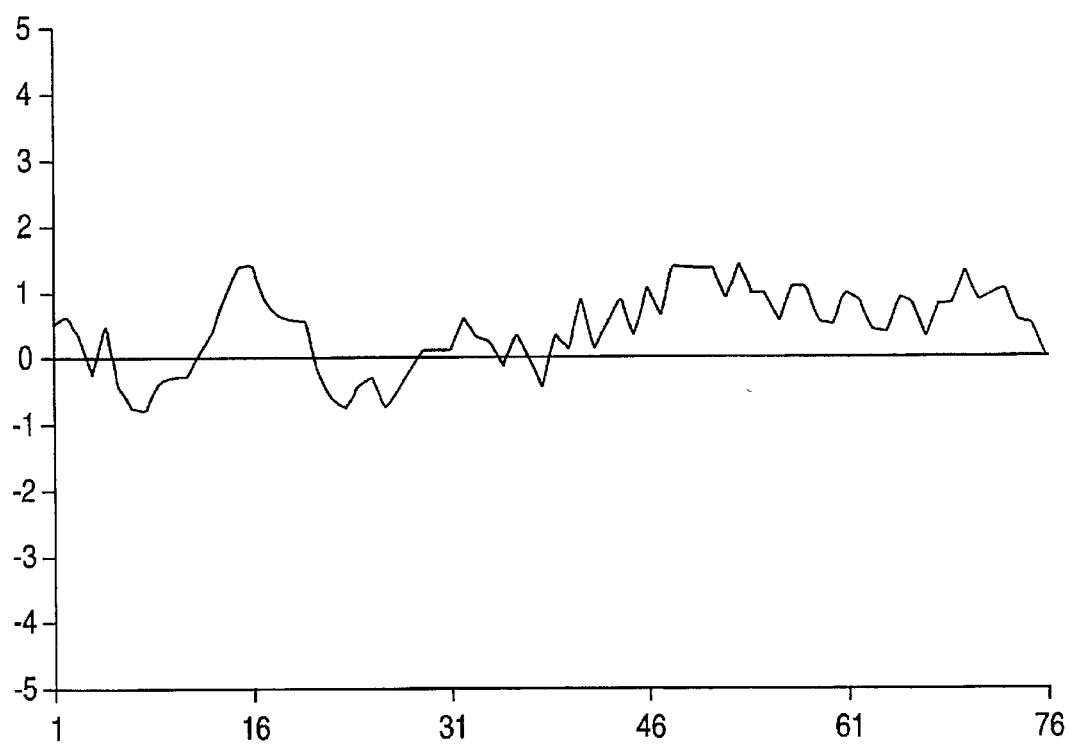

IPKA purified using PAGE electrophoresis (Sambrook, supra) is used to immunize rabbits and to produce antibodies using standard protocols. The amino acid sequence translated from IPKA is analyzed using DNAStar software (DNAStar Inc) to determine regions of high immunogenicity and a corresponding oligopolypeptide is synthesized and used to raise antibodies by means known to those of skill in the art. Analysis to select appropriate epitopes, such as those near the C-terminus or in hydrophilic regions is described by Ausubel F. M. et al (supra) and shown in FIGS. 4 and 5.

Typically, the oligopeptides are 15 residues in length, synthesized using an Applied Biosystems Peptide Synthesizer Model 431A using fmoc-chemistry, and coupled to keyhole limpet hemocyanin (KLH, Sigma) by reaction with M-maleimidobenzoyl-N-hydroxysuccinimide ester (MBS; Ausubel F. M. et al, supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

XI Purification of Naturally Occurring IPKA Using Specific Antibodies

Naturally occurring or recombinant IPKA is purified by immunoaffinity chromatography using antibodies specific for IPKA. An immunoaffinity column is constructed by covalently coupling IPKA antibody to an activated chromatographic resin such as CnBr-activated Sepharose (Pharmacia Biotech). After the coupling, the resin is blocked and washed according to the manufacturer's instructions.

Media containing IPKA is passed over the immunoaffinity column, and the column is washed under conditions that allow the preferential absorbance of IPKA (eg, high ionic strength buffers in the presence of detergent). The column is eluted under conditions that disrupt antibody/IPKA binding (eg, a buffer of pH 2–3 or a high concentration of a chaotrope such as urea or thiocyanate ion), and IPKA is collected.

XII Identification of Molecules Which Interact with IPKA

IPKA, or biologically active fragments thereof, are labelled with $^{125}$I Bolton-Hunter reagent (Bolton, A. E. and Hunter, W. M. (1973) Biochem J 133: 529). Candidate molecules previously arrayed in the wells of a 96 well plate are incubated with the labelled IPKA, washed and any wells with labelled IPKA complex are assayed. Data obtained using different concentrations of IPKA are used to calculate values for the number, affinity, and association of IPKA with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

---

We claim:

1. A purified polynucleotide encoding a polypeptide having an amino acid sequence shown in SEQ ID NO:2.

2. The polynucleotide of claim 1 wherein the nucleic acid sequence consists of SEQ ID NO:1, or its complement.

3. An expression vector comprising the polynucleotide of claim 1.

4. A host cell transformed with the expression vector of claim 3.

5. A method for producing a polypeptide consisting of the amino acid sequence shown in SEQ ID NO:2, the method comprising the steps of:

a) culturing the host cell of claim 4 to allow expression of the polypeptide; and b) recovering the polypeptide from the host cell culture.

* * * * *

SEQUENCE LISTING ( 1 ) GENERAL INFORMATION:

( i i i ) NUMBER OF SEQUENCES: 4

(2) INFORMATION FOR SEQ ID NO:1:

(i) SEQUENCE CHARACTERISTICS:
        (A) LENGTH: 545 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (vii) IMMEDIATE SOURCE:
        (A) LIBRARY: CERVNOT01
        (B) CLONE: 932876

(xi) SEQUENCE DESCRIPTION: SEQ ID NO:1:

```
TCCGCTGCGG GTTGCGGGCT GCGGGCGCTA GGCTGCCCCG GGGAGGCGCT GCGGACCGGC    60
GGCCCAGGCA CGGAGAGGCG GCGAGACCGC AGAATTCCCG TACTGATTAG TCAACAGTGG   120
AAAATCTGAA GAGATGCAAG CAGGAAAAAG AAATTAAACC AGGCCTGAGG AGCGATGCGA   180
CAGGCATGAT GGAGGTCGAG TCCTCCTACT CGGACTTCAT CTCCTGTGAC CGGACAGGCC   240
GTCGGAATGC GGTCCCTGAC ATCCAGGGAG ACTCAGAGGC TGTGAGCGTG AGGAAGCTGG   300
CTGGAGACAT GGGCGAGCTG GCACTCGAGG GGCAGAAGG ACAGGTGGAG GGAAGCGCCC    360
CAGACAAGGA AGCTGGCAAC CAGCCCCAGA GCAGCGATGG GACCACCTCG TCTTGAATCT   420
GACCTTGTCC AAGAAGGCTG GACGAGAGAC CTTCTGTCCC CTCCCAGAGG GGGAACCCTG   480
GCACTGGCCC AGCAGCCTCT TCTCTGAGCT CCATGTCCCA GATAAACCAG GCCAGACTGA   540
GAAGG                                                               545
```

(2) INFORMATION FOR SEQ ID NO:2:

(i) SEQUENCE CHARACTERISTICS:
        (A) LENGTH: 76 base pairs
        (B) TYPE: amino acid
        (C) STRANDEDNESS: single
        (D) TOPOLOGY: linear (ii) MOLECULE TYPE: cDNA (iii) HYPOTHETICAL: NO (vii) IMMEDIATE SOURCE:
        (A) LIBRARY: CERVNOT01
        (B) CLONE: 932876

(xi) SEQUENCE DESCRIPTION: SEQ ID NO:2:

```
Met Met Glu Val Glu Ser Ser Tyr Ser Asp Phe Ile Ser Cys Asp Arg
 1               5                  10                  15
Thr Gly Arg Arg Asn Ala Val Pro Asp Ile Gln Gly Asp Ser Glu Ala
                20                  25                  30
Val Ser Val Arg Lys Leu Ala Gly Asp Met Gly Glu Leu Ala Leu Glu
                35                  40                  45
Gly Ala Glu Gly Gln Val Glu Gly Ser Ala Pro Asp Lys Glu Ala Gly
                50                  55                  60
Asn Gln Pro Gln Ser Ser Asp Gly Thr Thr Ser Ser
65                  70                  75
```

(2) INFORMATION FOR SEQ ID NO:3:

(i) SEQUENCE CHARACTERISTICS:
        (A) LENGTH: 76 amino acids
        (B) TYPE: amino acid
        (C) STRANDEDNESS: single
        (D) TOPOLOGY: linear ( i i ) MOLECULE TYPE: peptide ( i i i ) HYPOTHETICAL: NO ( v i i ) IMMEDIATE SOURCE:
    ( A ) LIBRARY: CERVNOT01
    ( B ) CLONE: 932876

( x i ) SEQUENCE DESCRIPTION: SEQ ID NO:3:

```
Met Thr Asp Val Glu Ser Thr Tyr Ala Asp Phe Ile Ala Ser Gly Arg
 1               5                  10                 15

Thr Gly Arg Arg Asn Ala Leu His Asp Ile Leu Val Ser Ser Pro Gly
            20                  25              30

Gly Asn Ser Ser Glu Leu Ala Leu Lys Leu Ser Glu Leu Asp Ile Asn
        35              40                  45

Lys Ala Glu Gly Glu Gly Asp Ala Gln Arg Asn Pro Ser Glu Gln Thr
    50              55                  60

Gly Glu Ala Gln Gly Glu Ala Ala Lys Gln Glu Ser
 65             70                  75
```

( 2 ) INFORMATION FOR SEQ ID NO:4:

( i ) SEQUENCE CHARACTERISTICS:
        ( A ) LENGTH: 76 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v i i ) IMMEDIATE SOURCE:
        ( A ) LIBRARY: CERVNOT01
        ( B ) CLONE: 932876

( x i ) SEQUENCE DESCRIPTION: SEQ ID NO:4:

```
Met Thr Asp Val Glu Thr Thr Tyr Ala Asp Phe Ile Ala Ser Gly Arg
 1               5                  10                 15

Thr Gly Arg Arg Asn Ala Ile His Asp Ile Leu Val Ser Ser Ala Ser
            20                  25              30

Gly Asn Ser Asn Glu Leu Ala Leu Lys Leu Ala Gly Leu Asp Ile Asn
        35              40                  45

Lys Thr Glu Gly Glu Glu Asp Ala Gln Arg Ser Ser Thr Glu Gln Ser
    50              55                  60

Gly Glu Ala Gln Gly Glu Ala Ala Lys Ser Glu Ser
 65             70                  75
```